United States Patent
Tubman et al.

(10) Patent No.: US 10,179,115 B2
(45) Date of Patent: Jan. 15, 2019

(54) METHODS FOR TREATING MALARIA USING POTASSIUM CHANNEL INHIBITORS

(71) Applicant: THE CHILDREN'S MEDICAL CENTER CORPORATION, Boston, MA (US)

(72) Inventors: Venee Tubman, Jamaica Plain, MA (US); Carlo Brugnara, Boston, MA (US)

(73) Assignee: THE CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 15/552,027

(22) PCT Filed: Feb. 22, 2016

(86) PCT No.: PCT/US2016/018878
§ 371 (c)(1),
(2) Date: Aug. 18, 2017

(87) PCT Pub. No.: WO2016/134353
PCT Pub. Date: Aug. 25, 2016

(65) Prior Publication Data
US 2018/0042872 A1 Feb. 15, 2018

Related U.S. Application Data

(60) Provisional application No. 62/118,947, filed on Feb. 20, 2015.

(51) Int. Cl.
*A61K 31/165* (2006.01)
*A61K 31/045* (2006.01)
(Continued)

(52) U.S. Cl.
CPC .......... *A61K 31/165* (2013.01); *A61K 31/045* (2013.01); *A61K 31/4174* (2013.01); *A61K 31/4965* (2013.01); *Y02A 50/411* (2018.01)

(58) Field of Classification Search
None
See application file for complete search history.

(56) References Cited

U.S. PATENT DOCUMENTS 6,288,122 B1   9/2001   McNaughton-Smith et al.
6,331,564 B1   12/2001  Brugnara et al.
(Continued)

OTHER PUBLICATIONS

Tubman et al., Blood (2014), 124(21), pp. 743 (3 pages).*
(Continued)

*Primary Examiner* — Brian J Davis
(74) *Attorney, Agent, or Firm* — David S. Resnick; Nixon Peabody LLP

(57) ABSTRACT

The present invention relates to the field of anti-malarials. In particular, the disclosure relates to methods for treating malaria in a subject by administering to said subject a potassium channel inhibitor. The disclosed potassium channel inhibitors provide wide bioavailability, long half-life, and good toxicity profiles while showing high potency for killing parasites which cause malaria. In certain exemplary embodiments, the potassium channel inhibitor is an inhibitor of calcium-activated potassium channels. In certain exemplary embodiments, the potassium channel inhibitor is an inhibitor of the Gardos channel.

17 Claims, 6 Drawing Sheets

(51) Int. Cl.
 A61K 31/4174 (2006.01)
 A61K 31/4965 (2006.01)

(56) References Cited

U.S. PATENT DOCUMENTS

2011/0124735 A1 5/2011 Madsen et al.
2011/0300152 A1 12/2011 Li et al.

OTHER PUBLICATIONS

Hampton et al., Bioorganic & Medicinal Chemistry (2013), 21(18), pp. 5876-5885.*
Ataga et al., "Dose-Escalation Study of ICA-17043 in Patients with Sickle Cell Disease", Pharmacotherapy 26(11):1557-1564 (2006).
Brugnara C., "Sickle Cell Disease: From Membrane Pathophysiology to Novel Therapies for Prevention of Erythrocyte Dehydration", Journal of Pediatric Hematology/Oncology 25(12):927-933 (2003).
Foller et al., "Functional significance of the intermediate conductance Ca2+-activated K+ channel for the short-term survival of injured erythrocytes", Pflügers Archiv—European Journal of Physiology 460:1029-1044 (2010).
Waller et al., "Plasmodium falciparum: Growth response to potassium channel blocking compounds", Experimental Parasitology 120:280-285 (2008).
Allen et al., "Cell volume control in the Plasmodium-infected erythrocyte", Trends in Parasitology 20(1):7-10 (2004).
Ataga et al., "Efficacy and safety of the Gardos channel blocker, senicapoc (ICA-17043), in patients with sickle cell anemia", Blood 111(8):3991-3997 (2008).
Ataga et al., "Improvements in haemolysis and indicators of erythrocyte survival do not correlate with acute vaso-occlusive crises in patients with sickle cell disease: a phase III randomized, placebo-controlled, double-blind study of the gardos channel blocker senicapoc (ICA-17043)", British Journal of Haematology 153:92-104 (2011).
Cahalan et al., "The functional network of ion channels in T lymphocytes", Immunological Reviews 231(1):59-87 (2009).
Gemma et al., "Clotrimazole Scaffold as an Innovative Pharmacophore Towards Potent Antimalarial Agents: Design, Synthesis, and Biological and Structure-Activity Relationship Studies", Journal of Medicinal Chemistry 51(5):1278-1294 (2008).
Glushakova et al., "New Stages in the Program of Malaria Parasite Egress Imaged in Normal and Sickle Erythrocytes", Current Biology 20(12):1117-1121 (2010).
McNaughton-Smith et al., "Novel Inhibitors of the Gardos Channel for the Treatment of Sickle Cell Disease", Journal of Medicinal Chemistry 51(4):976-982 (2008).
Shmukler et al., "N-ethylmaleimide activates a Cl-independent component of K+ flux in mouse erythrocytes", Blood Cells, Molecules, and Diseases 51(1):9-16 (2013).
Stocker et al., "ICA-17043, a novel Gardos channel blocker, prevents sickled red blood cell dehydration in vitro and in vivo in SAD mice", Blood 101(6):2412-2418 (2003).
Tiffert et al., "Potent antimalarial activity of clotrimazole in in vitro cultures of Plasmodium falciparum", Proceedings of the National Academy of Sciences 97(1):331-336 (2000).
Tubman et al., "Seniacapoc, a Gardos Channel Inhibitor Developed to Treat Sickle Cell Disease, Exhibits Antimalrial Activity", Blood 124(21):743 (2014). (3 pages).

* cited by examiner

METHODS FOR TREATING MALARIA USING POTASSIUM CHANNEL INHIBITORS

CROSS REFERENCE TO RELATED APPLICATIONS

This application is a 371 National Phase Entry of International Patent Application No. PCT/US16/18878 filed on Feb. 22, 2016 which claims benefit under 35 U.S.C. § 119(e) of the U.S. Provisional Application No. 62/118,947, filed Feb. 20, 2015, the contents of both of which are incorporated herein by reference in their entireties.

GOVERNMENT SUPPORT

This invention was made with Government support under grant no. T32 HL007574 awarded by the National Heart, Lung, and Blood Institute (NHBLI) and grant no. R01 AI091787 awarded by the National Institute of Allergy and Infectious Diseases (NIAID). The government has certain rights in the invention.

TECHNICAL FIELD

The present invention relates to the field of anti-malarials. In particular, the disclosure relates to methods for treating malaria in a subject by administering to said subject a potassium channel inhibitor. The disclosed potassium channel inhibitors provide wide bioavailability, long half-life, and good toxicity profiles while showing high potency for killing parasites which cause malaria.

BACKGROUND

Despite significant therapeutic advances over the last 10 years, malaria still causes over 660,000 deaths annually. The *Plasmodium* parasites that cause malaria invade erythrocytes within which they mature as they digest hemoglobin. The proliferation of blood-stage parasites leads to an illness characterized by fever, hemolysis resulting in severe anemia and, in some cases, the neurologic and metabolic complications of cerebral malaria. As resistance to known antimalarial agents spreads, efforts to identify critical new targets to aid the development of novel antimalarial agents grow in importance.

Intracellular ion homeostasis of erythrocytes is important to the pathogenesis of sickle cell disease (SCD) and of malaria. The Gardos channel (KCNN4/IK-1) is a calcium-activated potassium channel expressed in a variety of tissues including hematopoietic tissues, lung, and colon. It is inactive in normal, resting erythrocytes, but is abnormally activated in sickle erythrocytes. Senicapoc, a Gardos channel inhibitor, prevents erythrocyte dehydration in SCD. It has effectively reduced disease severity in murine models of SCD and improved anemia in early phase clinical trials in patients with SCD. Administration of senicapoc to patients with SCD was well tolerated and reduced hemolysis through attenuation of sickle red cell dehydration, but failed to reduce the frequency of vaso-occlusive pain crises (Ataga K I et al. Br J Haematol 2011; 153:92-104).

Red cell volume regulation is critical both to the pathology of sickle cell disease and to the growth of *Plasmodium*, the parasites that cause malaria, since *Plasmodium* depends upon ion flow across the host membrane for growth (Glushakova S et al. Curr Biol 2010; 20:1117-1121). Cellular volume regulation also modulates the host defense against malaria infection. The process of intra-erythrocyte parasite maturation and eventual erythrocyte rupture synchronizes parasite swelling with erythrocyte potassium loss and sodium gain, leading to host cell rupture. As parasites mature, parasite-derived ion and nutrient channels insert into the host erythrocyte membrane, facilitating continued growth of the parasite. Parasite growth is impaired in dense, dehydrated sickle erythrocytes.

SUMMARY

The invention is directed to methods for treating malaria in a subject, comprising administering to said subject a therapeutically effective amount of a potassium channel inhibitor. In some embodiments, the potassium channel inhibitor may be selected from the group consisting of small molecules, peptides, proteins, nucleic acids, antibodies and any combination thereof. In certain exemplary embodiments, the potassium channel inhibitor is an inhibitor of calcium-activated potassium channels. In certain exemplary embodiments, the potassium channel inhibitor is an inhibitor of the Gardos channel.

DETAILED DESCRIPTION

It has been found that inhibitors of erythrocyte volume regulation function as antimalarial agents. Certain exemplary embodiments of the present invention provide a method of treating or preventing malaria. The method comprises administering to a subject suffering malaria a therapeutically effective amount of a potassium channel inhibitor. In certain exemplary embodiments, the potassium channel inhibitor is an inhibitor of calcium-activated potassium channels. In certain exemplary embodiments, the potassium channel inhibitor is an inhibitor of the Gardos channel. The Gardos channel is otherwise known as $KCNN_4$ or IK-1.

In some embodiments, the potassium channel inhibitor is a compound of Formula (I):

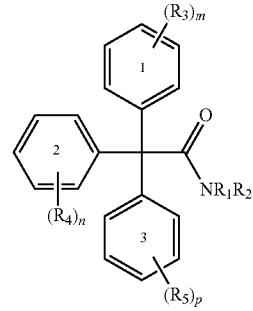

Formula (I)

wherein:

$R_1$ and $R_2$ are independently H or alkyl;

m, n and p are independently 0 or 1, provided that at least one of m, n and p is 1;

$R_3$, $R_4$ and $R_5$ are independently halogen, alkyl, alkenyl, alkynyl or alkoxy; and any stereoisomer, solvate or pharmaceutically acceptable salt thereof.

In some embodiments, the potassium channel inhibitor is senicapoc (2,2-bis(4-fluorophenyl)-2-phenylacetamide).

BRIEF DESCRIPTION OF THE DRAWINGS

FIG. 1 is a line graph showing concentration dependence of senicapoc-mediated growth inhibition of *P. falciparum* 3D7 over one asexual cycle. This nonlinear regression curve is representative of seven assays, each performed in triplicate.

FIG. 2 is a line graph showing senicapoc (2,2-bis(4-fluorophenyl)-2-phenylacetamide) rapidly kills parasites in the latter stages of the asexual cycle. Arrows mark the time of addition of the drug. Parasitemia was determined by flow cytometry and confirmed with microscopy (not shown). Error bars are present within the data points. Data presented are representative of three replicates.

FIG. 3 is a line graph showing senicapoc activity occurs in the later stages of the asexual parasite cycle as measured by nucleic acid replication. Mean fluorescence intensity (WI), determined by flow cytometry, is shown as a measure of parasite viability. Error bars are present within the data points. The data point for "No drug" at 48 h was gated for schizonts only (20% of infected cells) to eliminate signal from reinvaded ring-stage parasites. Data for other time points were not gated, as schizonts represented 5% of infected cells.

FIG. 4 is a scatter plot showing structure function analysis of senicapoc congeners demonstrating that antimalarial activity is independent of Gardos activity and identifies important conserved structural elements. The scales for the axes differ because the Gardos assays were performed in serum-free medium and senicapoc is highly protein bound.

FIG. 5 shows chemical structures of senicapoc and congeners with similar antimalarial activity.

FIG. 6 is a line graph showing senicapoc demonstrates prophylactic activity against parasites in an in vivo murine model. C57BL/6 mice infected with *P. yoelii* 17X-NL were treated by gavage with vehicle or senicapoc 400 or 800 mg/kg daily from days 2 to 10 post-infection (highlighted area) to mimic a preventive therapy.

FIG. 7 is a line graph showing senicapoc suppressed parasite growth in an in vivo murine model following established infection. C57BL/6 mice infected with *P. yoelii* 17X-NL were treated with vehicle or senicapoc 400 mg/kg twice daily from day 8 to day 15 postinfection (highlighted area) to mimic treatment of an active infection.

FIG. 8 is a line graph showing malaria infection is sustained independent of Gardos activity in an in vivo murine model. IK-1$^{-/-}$ and IK-1$^{+/+}$ mice were treated with vehicle twice daily on postinoculation days 8 to 15 (highlighted area).

FIG. 9 is line graph showing senicapoc suppression of malaria infection is independent of Gardos activity in an in vivo murine model. IK-1$^{-/-}$ and IK-1$^{+/+}$ mice were treated with senicapoc twice daily on postinoculation days 8 to 15 (highlighted area).

DETAILED DESCRIPTION

Figure 1:
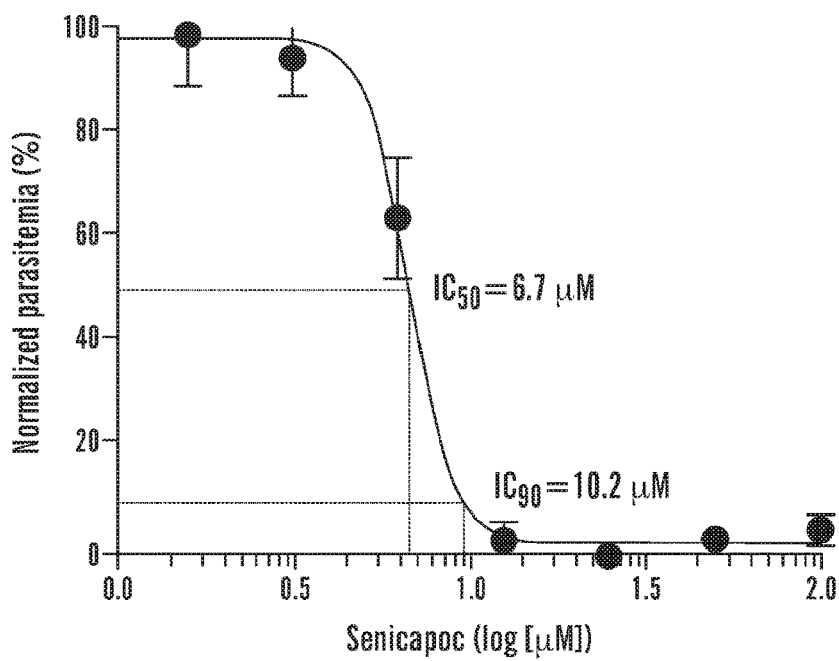
FIGS. 1-9 show that treatment with senicapoc effectively impairs parasite growth in vivo and in vitro.

It has been found that inhibitors of erythrocyte volume regulation function as antimalarial agents. Certain exemplary embodiments of the present invention provide a method of treating or preventing malaria. The method comprises administering to a subject suffering malaria a therapeutically effective amount of a potassium channel inhibitor. In certain exemplary embodiments, the potassium channel inhibitor is an inhibitor of calcium-activated potassium channels. In certain exemplary embodiments, the potassium channel inhibitor is an inhibitor of the Gardos channel. The Gardos channel is otherwise known as KCNN$_4$ or IK-1.

In a first aspect, the potassium channel inhibitor is a compound of Formula (I):

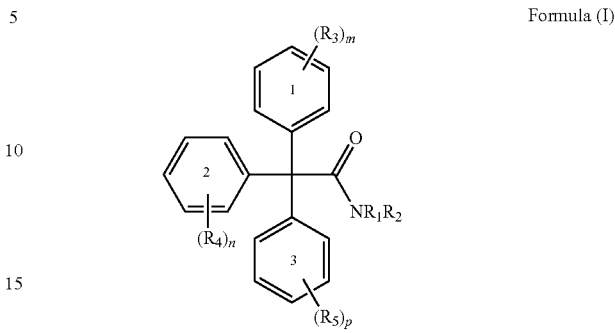

Formula (I)

wherein:
m, n and p are independently 0 or 1, provided that at least one of m, n and p is 1;
$R_1$ and $R_2$ are independently H or alkyl;
$R_3$, $R_4$ and $R_5$ are independently halogen, alkyl, alkenyl, alkynyl or alkoxy; and
any stereoisomer, solvate or pharmaceutically acceptable salt thereof.

In the various embodiments, m and n are 1; m and p are 1; or n and p are 1. In some other embodiments, m and n are 1 and p is 0; m and p are 1 and n is 0; or n and p are 1 and m is 0. In some embodiments, m, n and p all are 1.

Without limitations, $R_1$ and $R_2$ can be same or different. Thus, in some embodiments, $R_1$ and $R_2$ are same. In some other embodiments, $R_1$ and $R_2$ are different.

Exemplary alkyl groups for $R_1$ and $R_2$ include, but are not limited to, $C_1$-$C_6$ alkyl groups. Some specific exemplary alkyl groups for $R_1$ and $R_2$ include, but are not limited to, methyl, ethyl and propyl.

In some embodiments, $R_1$ and $R_2$ are independently selected from H, methyl, ethyl and propyl.

In some embodiments, at least one of $R_1$ and $R_2$ is H. In some further embodiments of this, both of $R_1$ and $R_2$ are H.

In various embodiments, $R_3$, $R_4$ and $R_5$ can be selected independently from the group consisting of halogen, $C_1$-$C_6$alkyl, $C_1$-$C_6$alkenyl, $C_1$-$C_6$alkynyl, $C_1$-$C_6$alkoxy.

In certain embodiments, $R_3$, $R_4$ and $R_5$ are independently F, Cl, Br or I.

In some embodiments, at least one (e.g., one, two or three) of $R_3$, $R_4$ and $R_5$ is F. In some embodiments, at least one (e.g., one, two or three) of $R_3$, $R_4$ and $R_5$ is Cl.

Exemplary alkyl groups for $R_3$, $R_4$ and $R_5$ include, but are not limited to, $C_1$-$C_6$ alkyl groups. Some specific exemplary alkyl groups for $R_3$, $R_4$ and $R_5$ include, but are not limited to, methyl, ethyl and propyl. In some embodiments, at least one (e.g., one, two or three) of $R_3$, $R_4$ and $R_5$ is $C_1$-$C_6$ alkyl. In some embodiments, at least one (e.g., one, two or three) of $R_3$, $R_4$ and $R_5$ is methyl.

Exemplary alkoxy groups for $R_3$, $R_4$ and $R_5$ include, but are not limited to, $C_1$-$C_6$ alkoxy groups. Some specific exemplary alkxoygroups for $R_3$, $R_4$ and $R_5$ include, but are not limited to, methoxy, ethoxy and propoxy. In some embodiments, at least one of $R_3$, $R_4$ and $R_5$ is a $C_1$-$C_6$ alkoxy. In some embodiments, at least one (e.g., one, two or three) of $R_3$, $R_4$ and $R_5$ is methoxy.

In some embodiments, at least one (e.g., one or two) of $R_3$, $R_4$ and $R_5$ is a halogen and at least one (e.g., one or two) of $R_3$, $R_4$ and $R_5$ is a $C_1$-$C_6$ alkyl. In some embodiments, at least one (e.g., one or two) of $R_3$, $R_4$ and $R_5$ is F and at least one (e.g., one or two) of $R_3$, $R_4$ and $R_5$ is methyl.

It is noted that each of $R_3$, $R_4$ and $R_5$ can independently located at a position ortho, meta or para to the acetamide substituent. In some embodiments, at least one of $R_3$, $R_4$ and $R_5$ is located at a position ortho to the acetamide substituent. In some embodiments, at least two of $R_3$, $R_4$ and $R_5$ are located at a position ortho to the acetamide substituent. In some embodiments, all three of $R_3$, $R_4$ and $R_5$ are located at a position ortho to the acetamide substituent.

In some embodiments, at least one of $R_3$, $R_4$ and $R_5$ is located at a position para to the acetamide substituent. In some embodiments, at least two of $R_3$, $R_4$ and $R_5$ are located at a position para to the acetamide substituent. In some embodiments, all three of $R_3$, $R_4$ and $R_5$ are located at a position para to the acetamide substituent.

In some embodiments, at least one of $R_3$, $R_4$ and $R_5$ is located at a position meta to the acetamide substituent. In some embodiments, at least two of $R_3$, $R_4$ and $R_5$ are located at a position meta to the acetamide substituent. In some embodiments, all three of $R_3$, $R_4$ and $R_5$ are located at a position meta to the acetamide substituent.

In some embodiments, at least one of at least one of $R_3$, $R_4$ and $R_5$ is located at a position para to the acetamide substituent and at least one of $R_3$, $R_4$ and $R_5$ is located at a position ortho to the acetamide substituent. In some embodiments, a compound of Formula (I) is a compound of Formula (II):

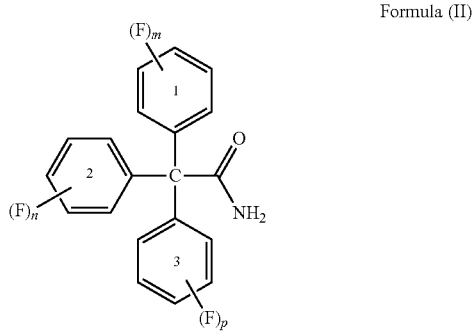

Formula (II)

wherein:
m, n and p are independently 0 or 1, provided that at least one of m, n and p is 1; and
any stereoisomer, solvate or pharmaceutically acceptable salt thereof.

In various embodiments, when m, n and p are all 1 in compounds of Formula (II), the fluoro substituents at ring 1 and at ring 2 are located at a position independently selected from ortho to the acetamide substituent, meta to the acetamide substituent and para to the acetamide substituent, and the substituent at ring 3 is at a position selected from ortho to the acetamide substituent para to the acetamide substituent.

In various compounds of Formula (II), when p is 0, and m is 1 and n is 1, the fluoro substituent at ring 1 is para to the acetamide substituent, and the substituent at ling 2 is located at a position selected from ortho to the acetamide substituent and para to the acetamide substituent.

In some embodiments, a compound of Formula (II) is a compound of Formula (III):

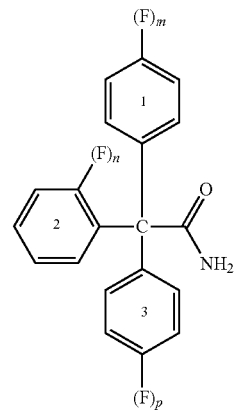

Formula (III)

wherein:
m, n and p are independently 0 or 1, provided that at least one of m, n and p is 1; and
any stereoisomer, solvate or pharmaceutically acceptable salt thereof.

In some embodiments, a compound of Formula (III) is a compound of Formula (IV):

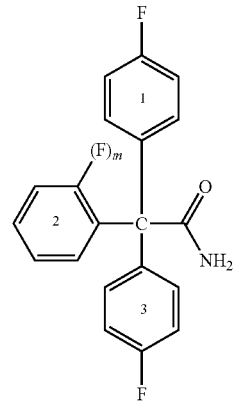

Formula (IV)

wherein:
m is either 0 or 1; and
any stereoisomer, solvate or pharmaceutically acceptable salt thereof.

Compounds of Formulas (I)-(IV) are described in U.S. Pat. No. 6,288,122, the content of which is incorporated herein by reference in its entirety.

In some embodiments, the potassium channel inhibitor is selected from the group consisting of:

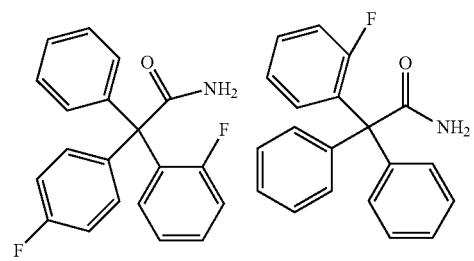

-continued

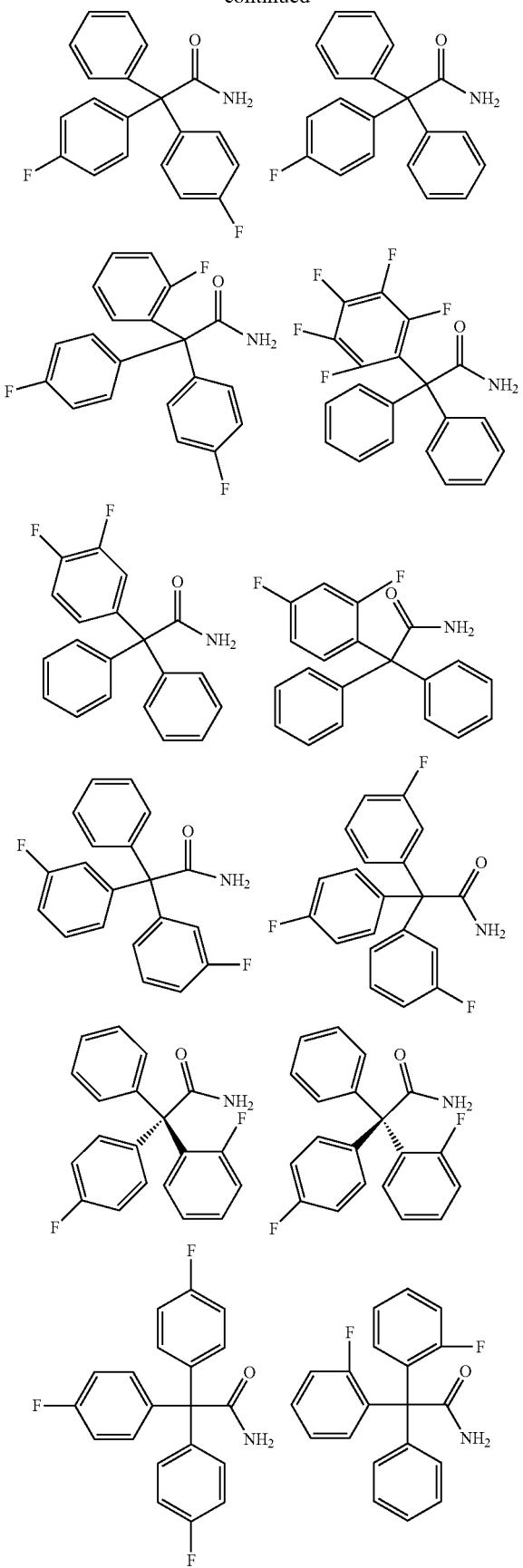

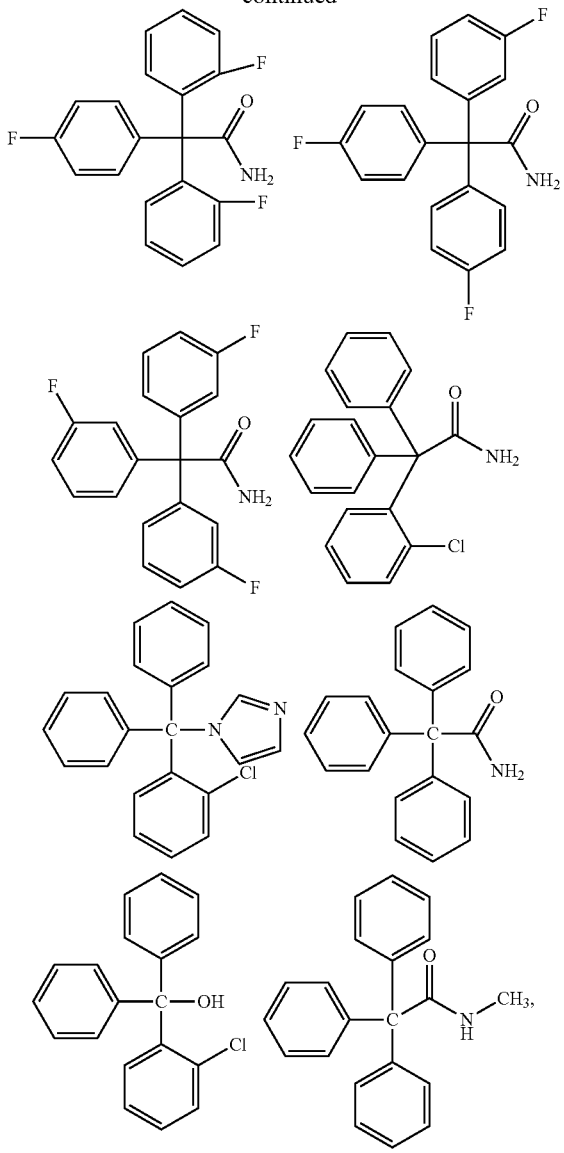

and
any stereoisomer, solvate or pharmaceutically acceptable salt thereof.

In another aspect, the present invention provides a method of inhibiting potassium flux of a cell. The method comprises contacting a cell with an amount of a compound according to Formula (I) effective to inhibit the potassium flux.

An important therapeutic pathway for treatment of malaria is preventing or retarding the dehydration of erythrocytes by manipulating the cellular ion fluxes of erythrocytes. Thus, in another aspect, the invention provides a method for reducing erythrocyte dehydration. The method comprises contacting an erythrocyte with an amount of a compound according to Formula (I) effective to reduce erythrocyte dehydration.

By "treating" or "treatment" of a disease or disorder is meant preventing the progression of the disorder or the condition described herein, altering the course of the disorder (for example, but are not limited to, slowing the progression of the disorder), reversing one or more symptoms of the disorder, or reducing one more symptoms, and/or one or more biochemical markers in a subject, preventing one or more symptoms from worsening or progressing, promoting recovery or improving prognosis. In some embodiments, the term "treating" as used herein can refer to prolonging survival as compared to expected survival if not receiving treatment. Thus, one of skill in the art realizes that a treatment can improve the disorder, but may not be a complete cure for the disorder. In some embodiments, the therapeutic treatment can refer to improved at least one function of an organ affected by the condition after administration of the composition described herein. In another embodiment, the therapeutic treatment can refer to alleviation or reduction of at least one symptom associated with the condition, e.g., angiogenic- or vascular-associated diseases. Measuring lessening includes any statistically significant decline in a measurable marker or symptom associated with the condition. In some embodiments, at least one symptom associated with a disorder or condition described herein can be alleviated or reduced by at least about 5%, at least about 10%, at least about 20%, at least about 30%, at least about 40%, at least about 50%, at least about 60%, at least about 70% or higher, relative to a subject without the administration of a composition described herein. In some embodiments, at least one symptom of associated with a disorder or condition described herein can be alleviated by at least about 80%, at least about 90%, at least about 95%, at least about 98% or higher, relative to a subject without the administration of a composition described herein. In one embodiment, at least one symptom associated with a disorder or condition described herein is alleviated by 100%, i.e. symptom-free.

As used herein, the term "preventing" with respect to a condition or disorder refers to delaying or preventing the onset of such disorder or condition described herein, e.g., in a subject at risk of having the condition. In some embodiments, "preventing" a condition can also encompass inhibiting, decreasing, or slowing the progression or severity of the condition, e.g., in a subject being diagnosed with the condition. The onset, the progression or severity of such disorder or condition can be determined by detecting an increase in at least one symptom associated with the condition, or a decrease in the function of the organ affected by the condition.

The phrase "therapeutically effective amount" as used herein refers to an amount of a compound described herein, or a composition comprising the compound, which is effective for producing some desired therapeutic effect in at least a sub-population of cells in a subject at a reasonable benefit/risk ratio applicable to any medical treatment. For example, a therapeutically effective amount of a compound or a composition comprising the compound can be an amount sufficient to produce a statistically significant, measurable change in at least one symptom of malaria described herein.

Determination of a prophylatically or therapeutically effective amount is well within the capability of those skilled in the art. Generally, a prophylatically or therapeutically effective amount can vary with the subject's history, age, condition, sex and risk factors, severity and type of the medical condition in the subject, and administration of other pharmaceutically active agents. Such amounts will depend on the particular condition being treated, the status of the condition and individual patient parameters including age, physical condition, size, weight, risk factors, and concurrent treatment. These factors are well known to those of ordinary skill in the art and can be addressed with no more than routine experimentation. In some embodiments, a maximum dose, that is, the highest safe dose according to sound medical judgment, can be used. In some embodiments, a lower dose or tolerable dose can be administered for medical reasons, psychological reasons or for virtually any other reasons. It is also well within the skill of the art to either start doses of the compound at levels lower than required to achieve the desired therapeutic effect and to gradually increase the dosage until the desired effect is achieved, or start doses of the compound at high levels and to gradually decrease the dosage until the desired effect is achieved, as appropriate for the care of the individual patient.

In some embodiments, the effective amount of the composition or the compound described herein can be sufficient to decrease or reduce at least one symptom associated with malaria by at least about 10%, at least about 20%, at least about 30%, at least about 40%, at least about 50%, at least about 60%, at least about 70% or higher, relative to that of a subject without the administration of the composition or the compound described herein, or a previous measurement obtained from the same subject being treated. In some embodiments, at least one symptom of associated with a disorder or condition described herein can be decreased by at least about 80%, at least about 90%, at least about 95%, at least about 98% or higher, relative to that of a subject without the administration of the composition or the compound described herein, or a previous measurement obtained from the same subject being treated. One of skill in the art is able to measure or diagnose the symptoms in accordance with each condition or disorder described herein.

In accordance with various embodiments provided herein, a subject in need thereof can be subjected to the treatment method described herein for any period of time. In some embodiments, the composition described herein can be administered to a subject for at least about 1 day, at least about 2 days, at least about 3 days, at least about 4 days, at least about 5 days, at least about 6 days, at least about 1 week, at least about 2 weeks, at least about 3 weeks, at least about 1 month or longer. In some embodiments, the composition described herein can be administered to a subject for at least about at least 2 months, at least about 3 months, at least about 4 months, at least about 5 months, at least about 6 months, at least about 7 months, at least about 8 months, at least about 9 months, at least about 10 months, at least about 11 months, at least about 12 months or longer. In other embodiments, the composition described herein can be administered to a subject in need thereof for at least about 1 year, at least about 2 years, at least about 3 years, at least about 4 years, at least about 5 years, at least about 6 years, or longer. In some embodiments, the composition described herein can be administered to a subject in need thereof until the condition is treated. In some embodiments, a subject in need thereof can continue to receive treatment for any period of time, e.g., days, weeks, months or years, after the condition or disorder is in remission. In such embodiment, the subject in need thereof can be administered with a lower dose of the composition after the condition is in remission. In some embodiments, a subject in need thereof can receive life-time administration of the composition described herein.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrastemal injection and infusion. In some embodiments, the compositions are administered by intravenous infusion or injection.

In some embodiments, the method further comprises co-administering one or more additional anti-malarial therapy to the subject. For example, co-administering an anti-malarial therapy already known in the art. As used herein, the term "co-administer" refers to administration of two or more therapies (e.g., potassium channel inhibitor and an additional anti-malarial therapy) within a 24 hour period of each other, for example, as part of a clinical treatment regimen. In other embodiments, "co-administer" refers to administration within 12 hours, within 6 hours, within 5 hours, within 4 hours, within 3 hours, within 2 hours, within 1 hour, within 45, within 30 minutes, within 20, within 15 minutes, within 10 minutes, or within 5 minutes of each other. In other embodiments, "co-administer" refers to administration at the same time, either as part of a single formulation or as multiple formulations that are administered by the same or different routes. When the potassium channel inhibitor and the additional anti-malarial therapy are administered in different pharmaceutical compositions or at different times, routes of administration can be same or different.

The frequency or the schedule of administering to a subject in need thereof a composition described herein can vary with various factors, including, but not limited to, modes of administration (e.g., oral or intravenous administration), dosage, severity of the condition to be treated, types of the condition to be treated, treatment type (e.g., preventive treatment or therapeutic treatment), and/or treatment regimen (e.g., administration of the composition alone or in combination with other clinical treatments). Accordingly, the time interval between any two consecutive administrations can vary, e.g., between hours, days, weeks, or months. In some embodiments, the time interval between any two consecutive administrations can be at least about 4 hours, at least about 6 hours, at least about 12 hours, at least about 24 hours, at least about 2 days, at least about 3 days, at least about 4 days, at least about 5 days, at least about 6 days, at least about 7 days or longer. In some embodiments, the time interval between any two consecutive administrations can be at least about 1 week, at least about 2 weeks, at least about 3 weeks, at least about 4 weeks or longer. In some embodiments, the time interval between any two consecutive administrations can be at least about 1 month, at least about 2 months, at least about 3 months, at least about 4 months, at least about 5 months, at least about 6 months or longer.

By way of example only, in some embodiments, the composition can be administered in pulses. Pulse therapy generally refers to a short, intensive administration of chemotherapy, usually given at intervals such as weekly or monthly. Individual pulses can be delivered to a patient continuously over a period of several hours, such as about 2 hours, 4 hours, 6 hours, 8 hours, 10 hours, 12 hours, 14 hours or 16 hours, or several days, such as 2 days, 3 days, 4 days, 5 days, 6 days, or 7 days. In some embodiments, individual pulses can be delivered to a patient continuously from about 1 hour to about 24 hours. In some embodiments, individual pulses can be delivered to a patient continuously from about 3 hours to about 9 hours.

In such embodiments, the time interval between pulses or the interval of no delivery can be greater than 24 hours or greater than 48 hours, and can be for even longer such as for 3 days, 4 days, 5 days, 6 days, 7 days, 8 days, 9 days or 10 days, two, three or four weeks or even longer. As the results achieved can vary, the time interval between pulses, when necessary, can be determined by one of ordinary skill in the art. Generally, the time interval between pulses can be determined based on the pharmacokinetics of the compound (e.g., half-life of the compound or the composition described herein). In some embodiments, another dose (pulse) of the composition can be administered when the composition or the active component of the composition from the previous dose falls below an effective range, e.g., the concentration of the compound in the blood or plasma is decreased by at least about 40%, at least about 50%, at least about 60%, at least about 70%, at least about 80%, at least about 90%, or higher, as compared to the initial concentration of the compound in the blood or plasma after administration. In some embodiments, another dose (pulse) of the composition can be administered when the composition or the compound from the previous dose is no longer detectable in the patient (e.g., the patient's blood sample). For example, the time intervals between pulses can be at least about the half-life of the composition or the compound disclosed herein, including at least about 2 times the half-life, at least about 3 times the half-life, at least about 4 times the half-life, at least about 5 times the half-life, at least about 10 times the half-life or longer, of the composition or the compound described herein.

The number of pulses in a single therapeutic regimen can be as little as two, but is typically from about 5 to 10, 10 to 20, 15 to 30 or more. In some embodiments, patients can receive the compositions or the compound described herein for life according to the methods provided herein. Compositions can be administered by any means, e.g., delivered to the patient as an injection (e.g. intravenous, subcutaneous, intra-arterial), infusion or instillation. Various methods and apparatus for pulsing compositions by infusion or other forms of delivery to the patient are disclosed in, but are not limited to, U.S. Pat. Nos. 4,747,825; 4,723,958; 4,948,592; 4,965,251 and 5,403,590.

In alternative embodiments, compositions comprising the compound described herein can be administered by sustained release, i.e., the composition or the compound described herein is released into the body slowly over an extended period of time. Sustained release can be accomplished by means of an osmotic pump or other delivery systems as described later. In such embodiments, the composition or the compound can be administered over any period of time, such as at least about 2 days, at least about 3 days, at least about 4 days, at least about 5 days, at least about 6 days, at least about 7 days, at least about 2 weeks, at least about 3 weeks, at least about 4 weeks, at least about 1 month, at least about 2 months, at least about 3 months or longer.

In some embodiments, a patient can be administered with a bolus of the composition described herein every 2 hours, every 4 hours, every 6 hours, every 12 hours, every 24 hours, every 2 days, every 3 days, every 4 days, every 5 days, every 6 days, every week or longer. Such administration can be performed by injection or orally. The term "bolus" as used herein refers to a single dose that is administered to a subject in less than 10 minutes, less than 5 minutes, less than 3 minutes, or shorter. The term "bolus" is generally intended to exclude dosage forms such as sustained release, pulsed release, and time release.

For administration to a subject, the compounds described herein can be provided in pharmaceutically acceptable compositions. These pharmaceutically acceptable compositions comprise a prophylatically- or therapeutically-effective amount of one or more of the compounds described above, formulated together with one or more pharmaceutically acceptable carriers (additives) and/or diluents. As described in detail below, the pharmaceutical compositions described herein can be formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes or gels; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly or intraocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960, the contents of which are incorporated by references in their entirety.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable carrier" refers to a pharmaceutically-acceptable material, composition or vehicle for administration of an active agent, e.g., a mutagenic compound. Pharmaceutically acceptable carriers include any and all solvents, dispersion media, coatings, antibacterial and antifungal agents, isotonic and absorption delaying agents, and the like which are compatible with the activity of the active agent and are physiologically acceptable to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" are used interchangeably herein.

When administering parenterally a pharmaceutical composition described herein, it can be generally formulated in a unit dosage injectable form (solution, suspension, emulsion). The pharmaceutical formulations suitable for injection include sterile aqueous solutions or dispersions. The carrier can be a solvent or dispersing medium containing, for example, water, buffers (e.g., phosphate buffered saline), polyol (for example, glycerol, propylene glycol, liquid polyethylene glycol, and the like), suitable mixtures thereof. In some embodiments, the pharmaceutical carrier can be a buffered solution (e.g. PBS).

An oral composition can be prepared in any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. Liquid preparations for oral administration can also be prepared in the form of a dry powder to be reconstituted with a suitable solvent prior to use.

In other embodiments, the compounds or compositions can be administered in the form of sustained-release or controlled-release formulations, e.g., to reduce repeated administration and inconvenience to the patient. Many types of delivery systems are available and known to those of ordinary skill in the art. They include, for example, polymer-based systems such as polylactic and/or polyglycolic acids, poly(lactic-co-glycolic acid), polyethylene glycol, polyanhydrides, poly(sebacic acid-co-ricinoleic acid), polycaprolactones, copolyoxalates, polyesteramides, polyorthoesters, polyhydroxybutyric acid, and/or combinations thereof. Microcapsules of some of the foregoing polymers containing drugs are described in, for example, U.S. Pat. No. 5,075,109. Accordingly, in some embodiments of the anti-vascular compositions, the compound or composition can be encapsulated in one or more polymeric vehicles such as microcapsules described above.

As described earlier, determination of a prophylatically or therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

If necessary, additives such as a preservative (e.g. benzyl alcohol, ethyl alcohol, benzalkonium chloride, phenol, chlorobutanol, etc.), an antioxidant (e.g. butylhydroxyanisole, propyl gallate, ascorbyl palmitate, alpha-tocopherol, etc.), and a thickener (e.g. lecithin, hydroxypropylcellulose, aluminum stearate, etc.) can be used in the compositions and formulations as disclosed herein.

In addition to the above-mentioned components, a stabilizer for further improving the stability of the compositions and formulations as disclosed herein, such as an antioxidant or a chelating agent, an isotonizing agent for adjusting the osmolarity, an auxiliary emulsifier for improving the emulsifying power, and/or an emulsion stabilizer for improving the stability of the emulsifying agent can be incorporated. The isotonizing agent that can be used includes, for example, glycerin, sugar alcohols, monosaccharides, disaccharides, amino acids, dextran, albumin, etc. These isotonizing agents can be used individually or in combination, with two or more. An emulsion stabilizer that can be used, which includes cholesterol, cholesterol esters, tocopherol, albumin, fatty acid amide derivatives, polysaccharides, polysaccharide fatty acid ester derivatives, etc.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Exemplary embodiments of the invention can be described by one or more of the following numbered paragraphs:

1. A method for treating malaria, comprising administering to a subject in need thereof a therapeutically effective amount of a potassium channel inhibitor.
2. The method of paragraph 1, wherein the potassium channel inhibitor is selected from the group consisting of small molecules, peptides, proteins, nucleic acids, antibodies and any combination thereof
3. The method of paragraph 1 or 2, wherein the potassium channel inhibitor is an inhibitor of calcium-activated potassium channels.
4. The method of any one of paragraphs 1-3, wherein the potassium channel inhibitor is an inhibitor of the Gardos channel.
5. The method of anyone of paragraphs 1-4, wherein the potassium channel inhibitor is a compound of Formula (I):

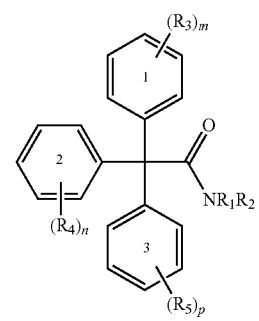

Formula (I)

wherein:
m, n and p are independently 0 or 1, provided that at least one of m, n and p is 1;
$R_1$ and $R_2$ are independently H or alkyl;
$R_3$, $R_4$ and $R_5$ are independently halogen, alkyl, alkenyl, alkynyl or alkoxy; and
any stereoisomer, solvate or pharmaceutically acceptable salt thereof.

6. The method of paragraph 5, wherein at least two of m, n and p are 1.
7. The method of paragraph 5 or 6, wherein all three of m, n and p are 1.
8. The method of anyone of paragraphs 5-7, wherein $R_1$ and $R_2$ are independently H or $C_1$-$C_6$ alkyl.
9. The method of anyone of paragraphs 5-8, wherein $R_1$ and $R_2$ are independently H, methyl, ethyl or propyl.
10. The method of anyone of paragraphs 5-9, wherein $R_1$ and $R_2$ are H.
11. The method of anyone of paragraphs 5-10, wherein at least one of $R_3$, $R_4$ and $R_5$ is a halogen.
12. The method of anyone of paragraphs 5-11, wherein at least one of $R_3$, $R_4$ and $R_5$ is an alkyl.
13. The method of paragraph anyone of paragraphs 5-12, wherein at least one of $R_3$, $R_4$ and $R_5$ is an alkoxy.
14. The method of anyone of paragraphs 5-13, wherein $R_3$, $R_4$ and $R_5$ are independently halogen, $C_1$-$C_6$alkyl or $C_1$-$C_6$alkoxy.
15. The method of anyone of paragraphs 5-14, wherein $R_3$, $R_4$ and $R_5$ are independently F, Cl, methyl or methoxy.
16. The method of paragraph 5, wherein the compound is of Formula (II):

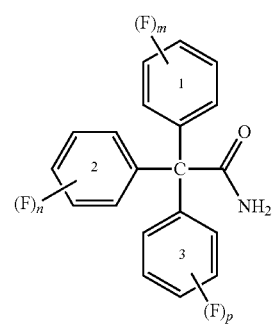

Formula (II)

wherein:
m, n and p are independently 0 or 1, provided that at least one of m, n and p is 1; and any stereoisomer, solvate or pharmaceutically acceptable salt thereof.

17. The method of paragraph 16, wherein the compound is of Formula

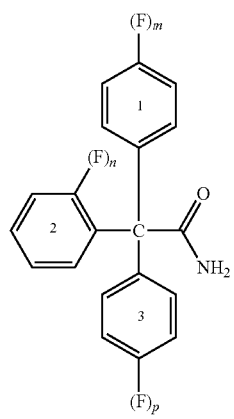

Formula (III)

wherein:
m, n and p are independently 0 or 1, provided that at least one of m, n and p is 1; and
any stereoisomer, solvate or pharmaceutically acceptable salt thereof.

18. The method of paragraph 7, wherein the compound is of Formula (IV):

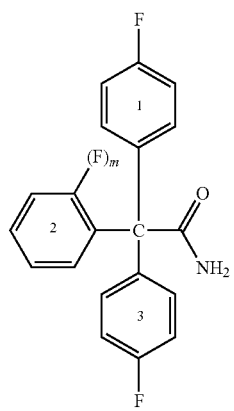

Formula (IV)

wherein:
m is either 0 or 1; and
any stereoisomer, solvate or pharmaceutically acceptable salt thereof.

19. The method of paragraph 1, wherein the potassium channel inhibitor is selected from the group consisting of:

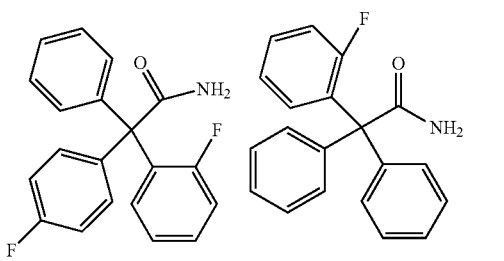

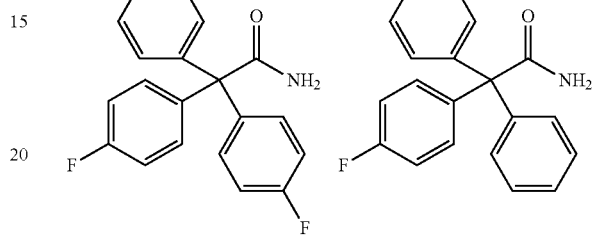

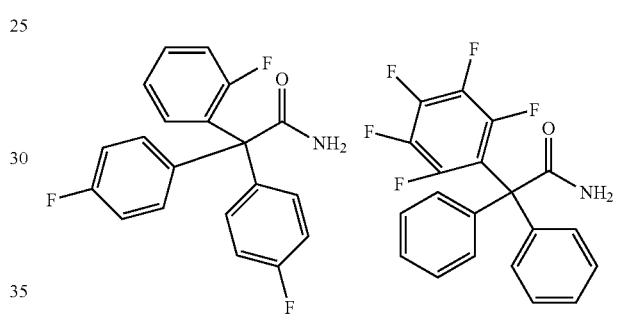

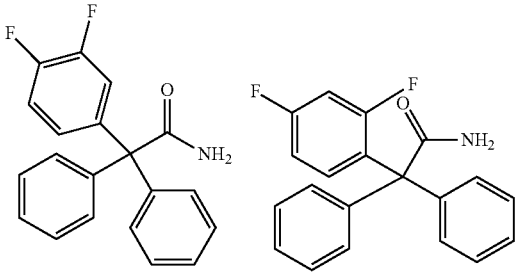

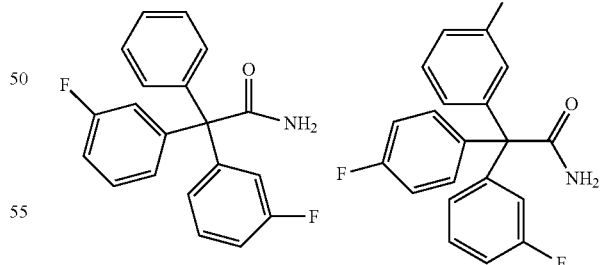

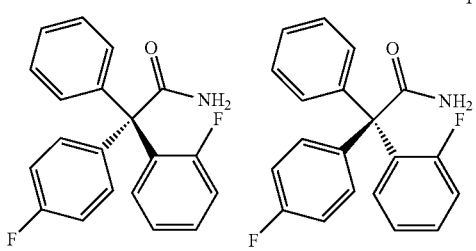

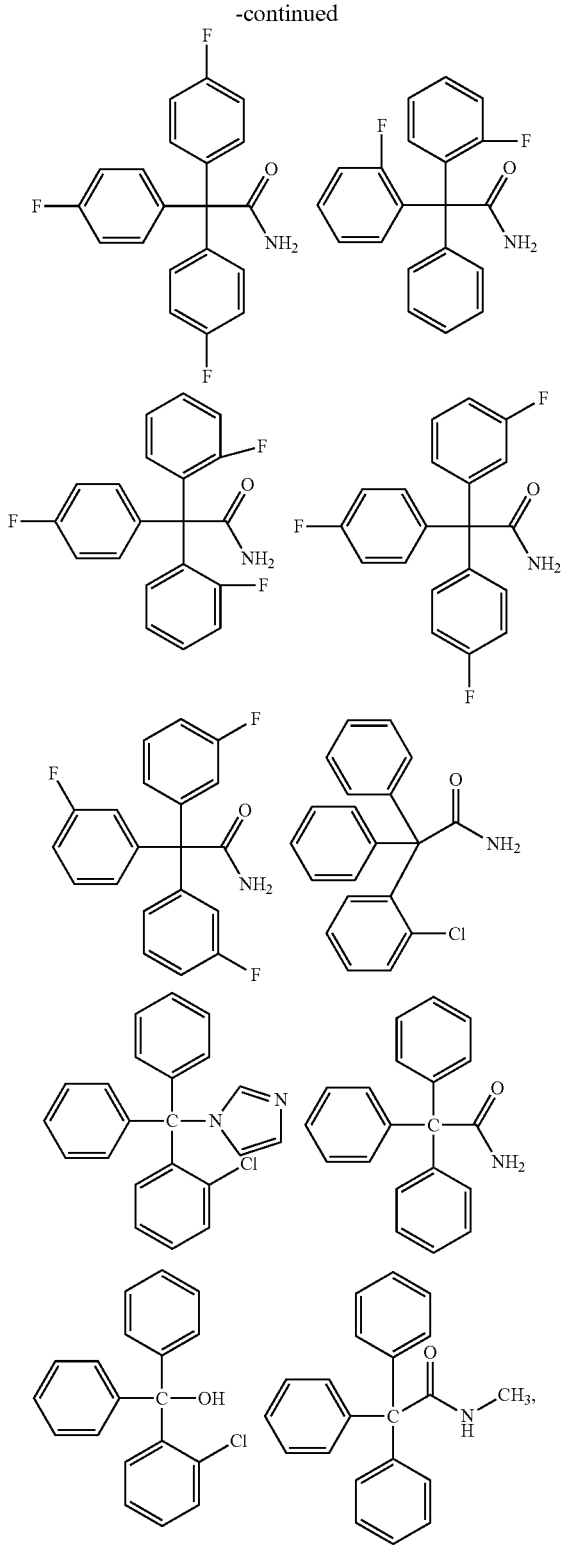

and any stereoisomer, solvate or pharmaceutically acceptable salt thereof

20. The method of paragraph 1, wherein the potassium channel inhibitor is senicapoc (2,2-bis(4-fluorophenyl)-2-phenylacetamide).

Some Selected Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are useful to an embodiment, yet open to the inclusion of unspecified elements, whether useful or not.

As used herein the term "consisting essentially of" refers to those elements required for a given embodiment. The term permits the presence of elements that do not materially affect the basic and novel or functional characteristic(s) of that embodiment of the invention.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

Other than in the operating examples, or where otherwise indicated, all numbers expressing quantities of ingredients or reaction conditions used herein should be understood as modified in all instances by the term "about." The term "about" when used in connection with percentages may mean±1% of the value being referred to. For example, about 100 means from 99 to 101.

The terms "subject" and "individual" are used interchangeably herein, and mean a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein. The terms, "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of cancer. In addition, the methods described herein can be used to treat domesticated animals and/or pets. A subject can be male or female. A subject can be one who has been previously diagnosed with or identified as suffering from cancer, but need not have already undergone treatment.

As used here in the term "isomer" refers to compounds having the same molecular formula but differing in structure. Isomers which differ only in configuration and/or conformation are referred to as "stereoisomers." The term "isomer" is also used to refer to an enantiomer.

The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate planepolarized light in different directions). Enantiomers generally have identical physical properties, such as melting points and boiling points, and also have identical spectroscopic properties. Enantiomers can differ from each other with respect to their interaction with plane-polarized light and with respect to biological activity.

The designations "R and S" are used to denote the absolute configuration of the molecule about its chiral center(s). The designations may appear as a prefix or as a suffix; they may or may not be separated from the isomer by a hyphen; they may or may not be hyphenated; and they may or may not be surrounded by parentheses. The artisan will notice that compounds of Formula (I) may comprise a chiral center at the carbon to which the phenyl groups are attached. Thus, the compounds of Formula (I) can be the R-isomer or the S-isomer or a mixture or R- and S-isomers.

As used herein, the term "alkyl" means a straight or branched, saturated aliphatic radical having a chain of carbon atoms. $C_x$ alkyl and $C_x$-$C_y$alkyl are typically used where X and Y indicate the number of carbon atoms in the chain. For example, $C_1$-$C_6$alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., $(C_6$-$C_{10})$aryl$(C_0$-$C_3)$alkyl includes phenyl, benzyl, phenethyl, 1-phenylethyl 3-phenylpropyl, and the like. Backbone of the alkyl can be optionally inserted with one or more heteroatoms, such as N, O, or S.

The term "alkyl" as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone.

As used herein, the term "alkenyl" refers to unsaturated straight-chain, branched-chain or cyclic hydrocarbon radicals having at least one carbon-carbon double bond. $C_x$ alkenyl and $C_x$-$C_y$alkenyl are typically used where X and Y indicate the number of carbon atoms in the chain. For example, $C_2$-$C_6$alkenyl includes alkenyls that have a chain of between 1 and 6 carbons and at least one double bond, e.g., vinyl, allyl, propenyl, isopropenyl, 1-butenyl, 2-butenyl, 3-butenyl, 2-methylallyl, 1-hexenyl, 2-hexenyl, 3-hexenyl, and the like). Alkenyl represented along with another radical (e.g., as in arylalkenyl) means a straight or branched, alkenyl divalent radical having the number of atoms indicated. Backbone of the alkenyl can be optionally inserted with one or more heteroatoms, such as N, O, or S. The alkenyl group can be substituted as described above for alkyl.

As used herein, the term "alkynyl" refers to unsaturated hydrocarbon radicals having at least one carbon-carbon triple bond. $C_x$ alkynyl and $C_x$-$C_y$alkynyl are typically used where X and Y indicate the number of carbon atoms in the chain. For example, $C_2$-$C_6$alkynyl includes alkynls that have a chain of between 1 and 6 carbons and at least one triple bond, e.g., ethynyl, 1-propynyl, 2-propynyl, 1-butynyl, iso-pentynyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. Backbone of the alkynyl can be optionally inserted with one or more heteroatoms, such as N, O, or S. The alkynyl group can be substituted as described above for alkyl.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy, n-propyloxy, iso-propyloxy, n-butyloxy, iso-butyloxy, and the like. The alkoxy group can be substituted as described above for alkyl.

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified.

In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, $CF_3$, cyano (CN), cycloalkyl, cycloalkylene, ester, ether, haloalkyl, halogen, halogen, heteroaryl, heterocyclyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

As used herein, the term "pharmaceutically-acceptable salts" refers to the conventional nontoxic salts or quaternary ammonium salts of therapeutic agents, e.g., from non-toxic organic or inorganic acids. These salts can be prepared in situ in the administration vehicle or the dosage form manufacturing process, or by separately reacting a therapeutic agent in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), content of which is herein incorporated by reference in its entirety.

In some embodiments of the aspects described herein, representative salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The technology described herein is further illustrated by the following examples which in no way should be construed as being further limiting.

EXAMPLES

Example 1: Antimalarial Effects of Senicapoc and Analogs

Intracellular ion homeostasis of erythrocytes is important in the pathogenesis of sickle cell disease (SCD) and malaria. Stemming potassium loss and cellular dehydration have been explored as therapeutic strategies to prevent sickling in SCD (Brugnara C. 2003. Sickle cell disease: from membrane pathophysiology to novel therapies for prevention of erythrocyte dehydration. J Pediatr He-matol Oncol 25:927-933). During intraerythrocyte maturation of *Plasmodium*, parasite swelling is coordinated with erythrocyte sodium gain and potassium loss, ultimately leading to erythrocyte rupture (Allen R J W, Kirk K. 2004. Cell volume control in the *Plasmodium*-infected erythrocyte. Trends Parasitol 20:7-10). Inhibitors of erythrocyte volume regulation have been hypothesized to function as antimalarial agents Waller K L, Kim K, McDonald T V. 2008. *Plasmodium falciparum*: growth response to potassium channel blocking compounds. Exp Parasitol 120: 280-285 and Tiffert T, Ginsburg H, Krugliak M, Elford B C, Lew V L. 2000. Potent antimalarial activity of clotrimazole in in vitro cultures of *Plasmodium falciparum*. Proc Natl Acad Sci USA 97:331-336).

The Gardos channel (KCNN4/IK-1) is a calcium-activated potassium channel abnormally active in sickle erythrocytes (McNaughton-Smith G A, Burns J F, Stocker J W, Rigdon G C, Creech C, Arrington S, Shelton T, de Franceschi L. 2008. Novel inhibitors of the Gardos channel for the treatment of sickle cell disease. J Med Chem 51: 976-982). In a phase 3 trial in patients with SCD, therapy with the Gardos channel inhibitor senicapoc improved physiological disease markers but failed to modify the frequency of vasoocclusive pain episodes (Ataga K I, Reid M, Ballas S K, Yasin Z, Bigelow C, James L S, Smith W R, Galacteros F, Kutlar A, Hull J H, Stocker J W. 2011. Improvements in haemolysis and indicators of erythrocyte survival do not correlate with acute vaso-occlusive crises in patients with sickle cell disease: a phase III randomized, placebo-controlled, double-blind study of the Gardos channel blocker senicapoc (ICA-17043). Br J Haematol 153:92-104). Senicapoc was well tolerated in human and animal studies for SCD (Ataga K I, Smith W R, De Castro L M, Swerdlow P, Saunthararajah Y, Castro O, Vichinsky E, Kutlar A, Orringer E P, Rigdon G C, Stocker J W. 2008. Efficacy and safety of the Gardos channel blocker, senicapoc (ICA-17043), in patients with sickle cell anemia. Blood 111:3991-3997 and Stocker J W, De Franceschi L, McNaughton-Smith G A, Corrocher R, Beuzard Y, Brugnara C. 2003. ICA-17043, a novel Gardos channel blocker, prevents sickled red blood cell dehydration in vitro and in vivo in SAD mice. Blood 101:2412-2418). Here, we report the effect of senicapoc on the growth of *Plasmodium*. The present study presents a path to a new antimalarial agent.

The in vitro 50% inhibitory concentration ($IC_{50}$) values of senicapoc and other antimalarials for inhibition of multiple strains of *Plasmodium falciparum* and *Plasmodium knowlesi* are shown in Table 1. Senicapoc demonstrated antimalarial activity against blood-stage *P. falciparum* 3D7 with an $IC_{50}$ of 6.7 M (FIG. 1). Comparable micromolar antimalarial activity was demonstrated against *P. falciparum* strains with varied antimalarial sensitivities. In all human *Plasmodium* strains tested, the $IC_{90}$ was <2-fold higher than the $IC_{50}$. $IC_{50}$s of reference antimalarials determined in parallel were in the nanomolar range (Table 1).

Senicapoc demonstrated a low micromolar $IC_{50}$ against the primate parasite *P. knowlesi*. To identify a relationship between senicapoc activity and human erythrocytes, *P. knowlesi* H1 cultured in rhesus erythrocytes and *P. knowlesi* YH-1 adapted for culture in human erythrocytes were each treated with senicapoc. There was no difference between the senicapoc $IC_{50}$s for H1 and YH-1 (P=0.14) (Table 1). Senicapoc was similarly effective against parasitized human and rhesus erythrocytes.

Figure 2:
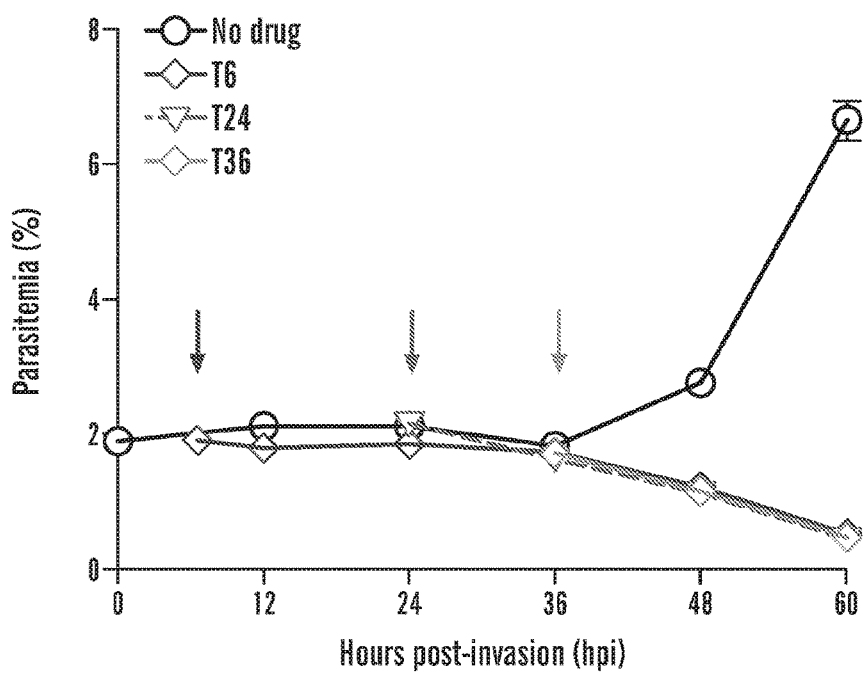
Figure 3:
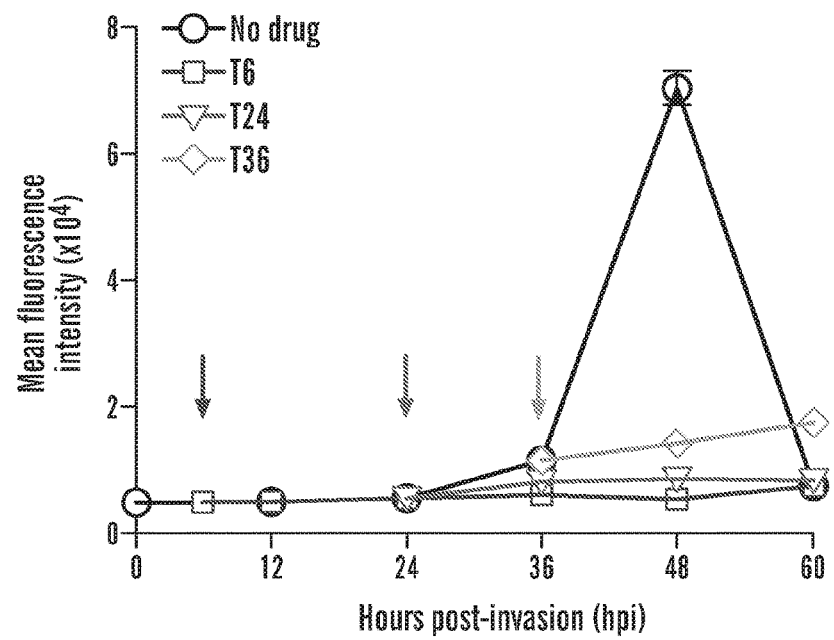

To determine senicapoc's activity through the 48-hour asexual blood stage of the parasite, growth inhibition of *P. falciparum* 3D7 was characterized throughout the cycle by microscopy and flow cytometry. Parasitemia measured by flow cytometry was reduced by 48 h postinvasion (hpi) in all treated cultures compared to that in the control (P<0.008) (FIG. 2). Parasites within treated cultures appeared smaller and failed to form a digestive vacuole by 36 hpi, followed by rapid parasite death (data not shown). Nucleic acid content measured by mean fluorescence intensity (MFI) was weaker in treated cultures at 36 h (P<0.008), and the expected rise in MFI through schizogony was absent (FIG. 3). Schizonts were not seen by microscopy (data not shown). These data indicate that senicapoc was effective during late, metabolically active stages of parasite development.

Figure 4:
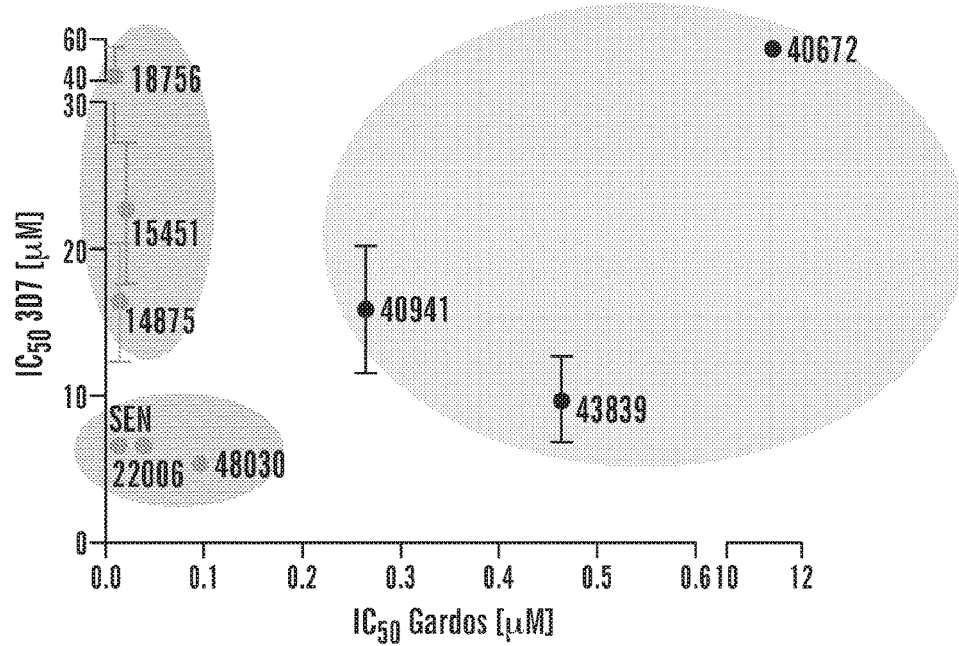
Figure 5:
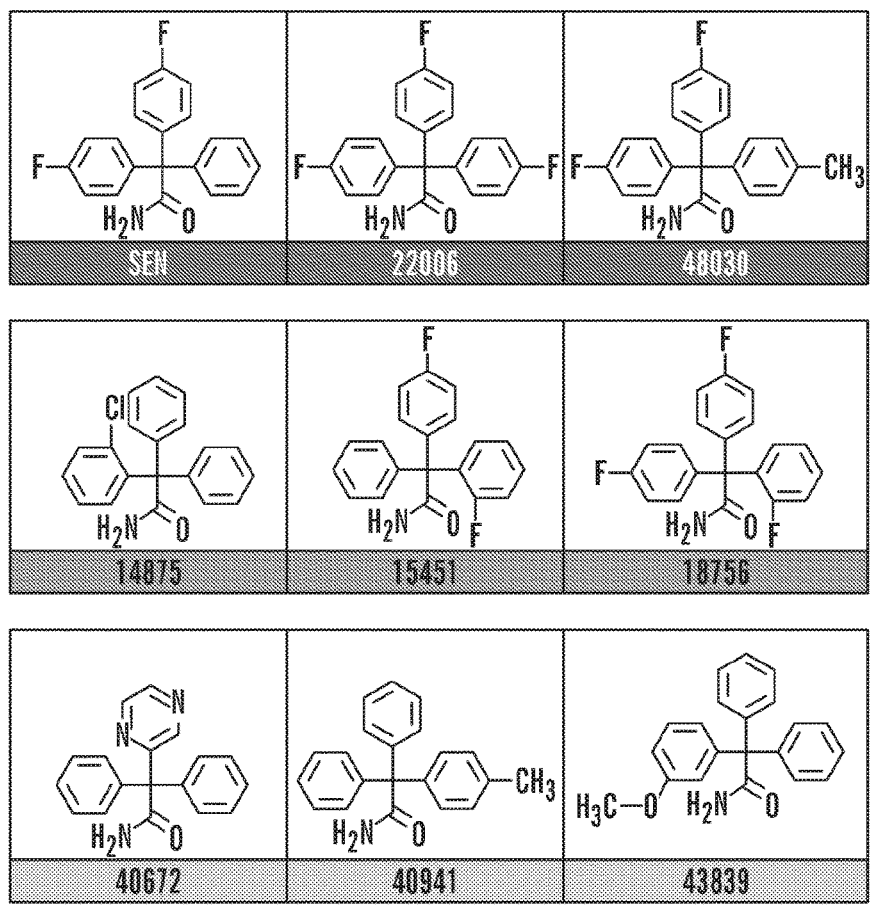

The inventors examined several senicapoc congeners and identified no relationship between the potency of Gardos inhibitory activity and antimalarial activity (FIG. 4). Thus, senicapoc may not specifically target the Gardos channel for its antimalarial activity. Interestingly, halogenation of the triarylmethyl group was related to inhibition of both parasite growth and the Gardos channel. Para-position halogens were associated with more potent inhibition of parasite growth and of the channel (FIG. 5). Unhalogenated compounds demonstrated the weakest antiparasite activity and Gardos inhibition (data not shown). Halogen substitution on the phenyl group has been shown to affect compound bioavailability and in vivo stability (5). The triarylmethyl group is important for antimalarial activity in clotrimazole (9). These structural clues may be important for optimization of the antimalarial activity of seni-capoc or its congeners.

Figure 6:
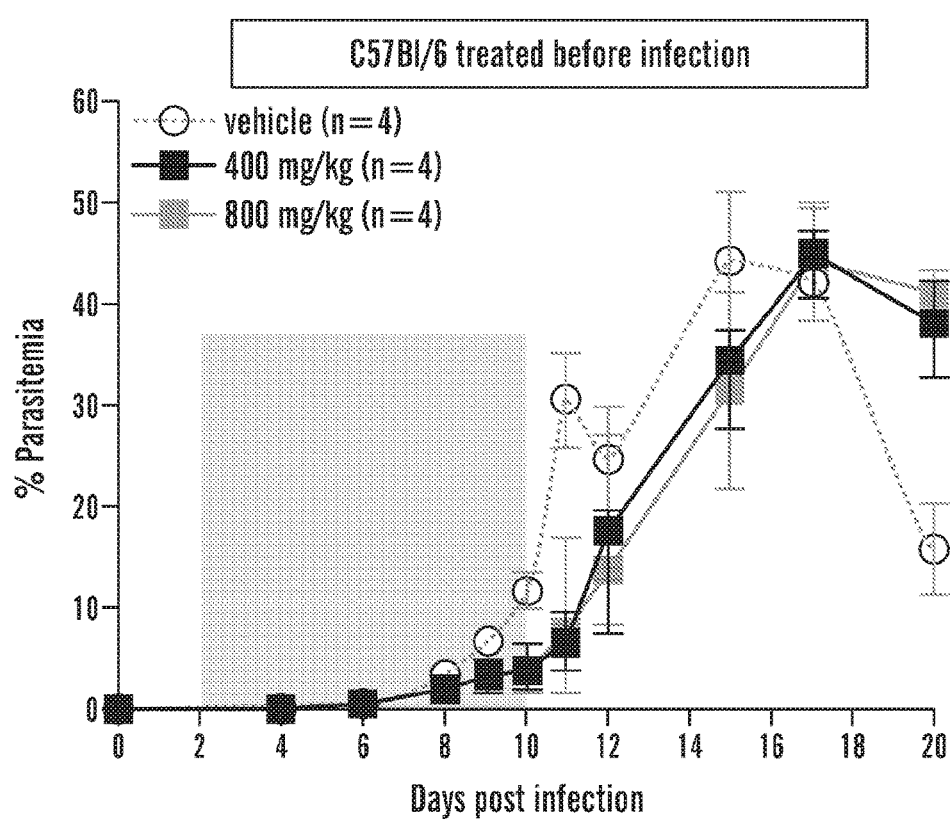
Figure 7:
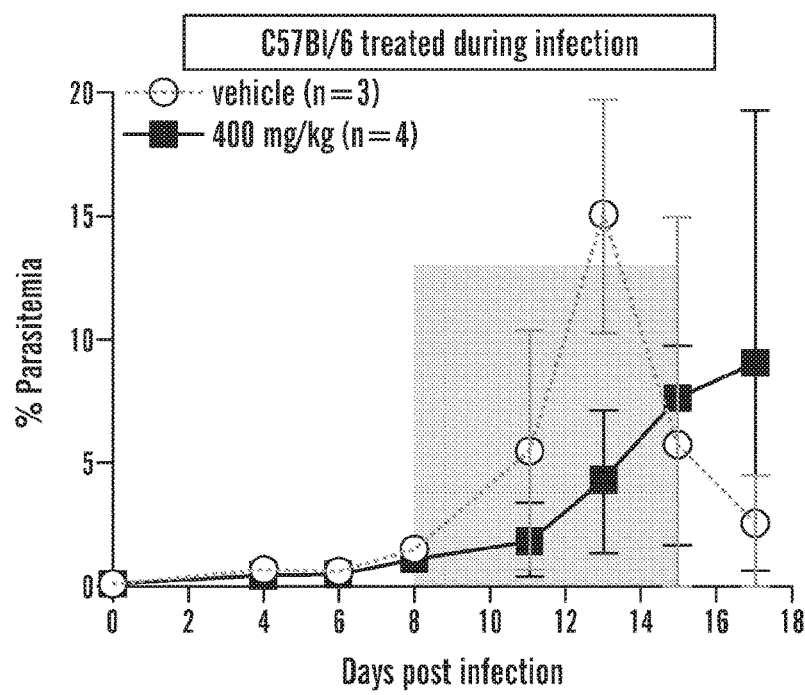

To establish in vivo efficacy against blood-stage parasites, C57BL/6 mice infected with *P. yoelii* 17X-NL (nonlethal strain) were treated with vehicle or senicapoc. (All experiments were performed under protocols approved by the institutional animal care and use committees of the Harvard School of Public Health and of Beth Israel Deaconess Medical Center.) The expected immune-mediated clearance of 17X-NL was observed in vehicle-treated mice beyond postinoculation day 15. C57BL/6 mice exhibited partial suppression of parasite growth during treatment. When senicapoc was given as prophylaxis on postinoculation days 2 to 10, treated mice demonstrated significantly lower parasitemia by day 10 than vehicle-treated mice (4.3% versus 12%; P=0.04). Parasitemia increased after the drug was stopped (FIG. 6). When senicapoc was given as treatment on postinoculation days 8 to 15, treated mice demonstrated lower parasitemia beyond day 13, but the difference was not statistically significant (P=0.058) (FIG. 7). Considering that the shorter half-life of senicapoc in mice compared to humans may impact its effect in the murine model (Stocker J W, De Franceschi L, McNaughton-Smith G A, Corrocher R, Beuzard Y, Brugnara C. 2003. ICA-17043, a novel Gardos channel blocker, prevents sickled red blood cell dehydration in vitro and in vivo in SAD mice. Blood 101:2412-2418), these data demonstrate antiparasite activity of senicapoc in vivo consistent with our in vitro results.

To test whether senicapoc targets the Gardos channel in malaria-infected erythrocytes, we assessed the ability of *P. yoe-lii* to grow in the presence and absence of the channel in vivo using a Gardos knockout ($IK-1^{-/-}$) mouse model (Shmukler B E, Hsu A, Alves J, Trudel M, Rust M B, Hubner C A, Rivera A, Alper S L. 2013. N-ethylmaleimide activates a Cl(−)-independent component of K(+) flux in mouse erythrocytes. Blood Cells Mol Dis 51:9-16 and Rifler M, Bobbala D, Koka S, Boini K M, Mahmud H, Kasinathan R S, Shumilina E, Amann K, Beranek G, Sausbier U, Ruth P, Sausbier M, Lang F, Huber S M. 2010. Functional significance of the intermediate conductance Ca2+-activated K+ channel for the short-term survival of injured erythrocytes.

TABLE 1

Antimalarial activity of senicapoc against *Plasmodium falciparum* and *Plasmodium knowlesi*

| | | | $IC_{50}$ (mean ± 95% confidence interval)[a] with: | | | | | |
|---|---|---|---|---|---|---|---|---|
| Species | Strain | Res | SEN (μM) | SEN (μM) $IC_{90}$ | CLT (μM) | MQ (nM) | DHA (nM) | CQ (nM) |
| *P. falciparum* | 3D7 | | 6.74 ± 0.25 | 10.17 ± 2.07 | 5.67 ± 1.11 | 10.11 ± 7.83 | 2.73 ± 1.55 | 15.55 ± 3.31 |
| | 7G8 | CQ | 10.88 ± 2.30 | 22.31 ± 9.52 | 2.46 ± 0.12 | 3.63 ± 0.58 | 1.65 ± 1.24 | 97.93 ± 20.43 |
| | W2mef | CQ, MQ | 9.24 ± 3.13 | 12.30 ± 1.82 | 8.92 ± 0.02 | 26.70 ± 15.53 | 5.16 ± 4.28 | 316.3 ± 135.27 |
| *P. knowlesi* | H1 | | 17.54 ± 6.74 | 31.36 ± 11.79 | | | | |
| | YH-1 | | 10.99 ± 1.38 | 37.43 ± 1.19 | | | | |

[a]Mean $IC_{50}$5 of senicapoc (SEN) against a panel of *P. falciparum* with varied resistance (Res) patterns (3D7, 7G8, W2mef) and *P. knowlesi* (H1, YH-1) are shown. 95% confidence intervals determined from at least three independent experiments performed in triplicate. CQ, chloroquine; CLT, clotrimazole; MQ, mefloquine; DHA, dihydroartemisinin.

Figure 8:
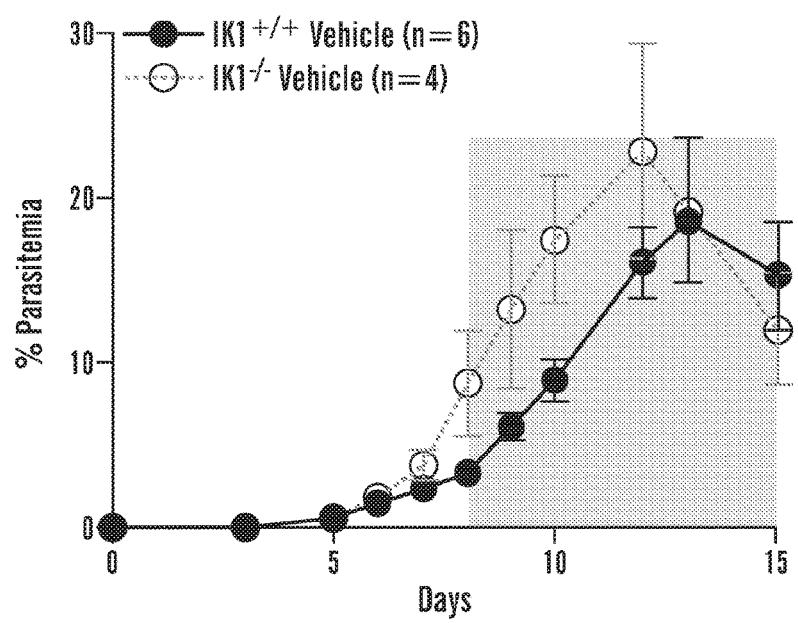
Figure 9:
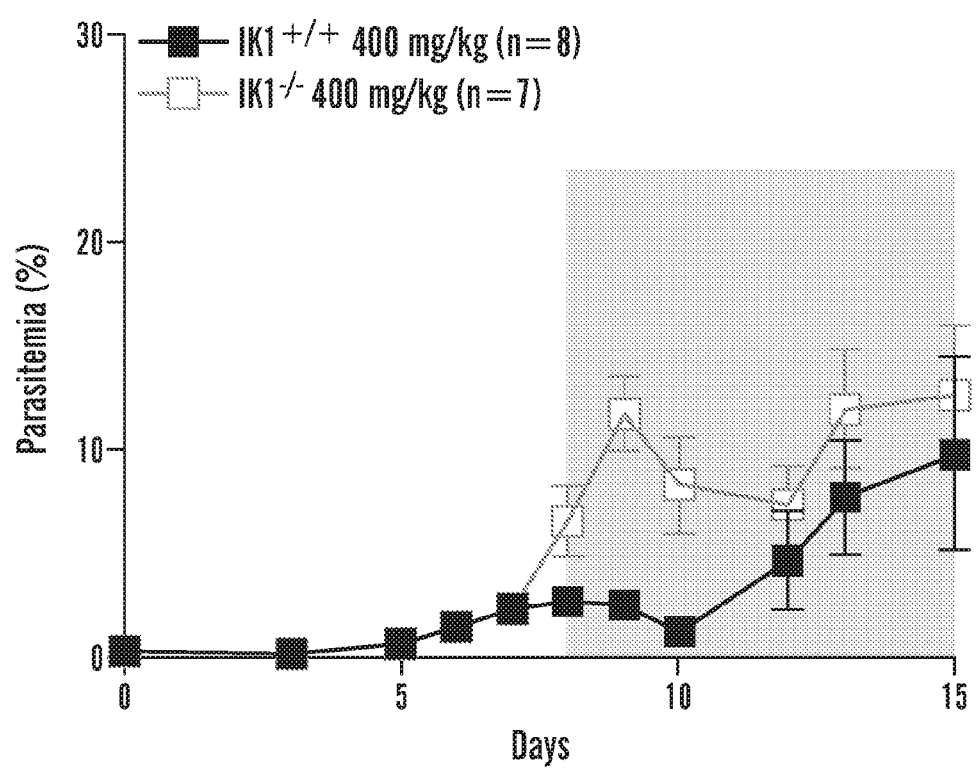

Pflugers Arch 460:1029-1044). Unexpectedly, accelerated parasite growth was evident in IK-1/mice by postinoculation day 7 (3.6% versus 2.2% in IK-1/mice; P 0.03) (FIG. 8). The discrepant kinetics of parasite growth in IK-1$^{-/-}$ and IK-1$^{+/+}$ mice is not understood but may reflect impaired immunity in addition to absence of the ion channel from erythrocytes. For example, absent Gardos channels in some T-cell subsets might contribute to delayed parasite clearance, countering the effect of Gardos channel inhibition on parasite growth in vivo (Cahalan M D, Chandy K G. 2009. The functional network of ion channels in T lymphocytes. Immunol Rev 231:59-87). The inventors then assessed the effectiveness of senicapoc in the presence and absence of the channel in vivo. *P. yoelii*-infected IK-1$^{-/-}$ and IK-1$^{+/+}$ mice were treated with senicapoc 400 mg/kg twice daily. Senicapoc was active against *P. yoelii* in IK-1$^/$ mice, indicating activity independent of the channel (FIG. 9).

It is noted that the whole-blood concentration required for in vitro inhibition of parasite growth against *P. falciparum* was an order of magnitude higher than the peak concentrations achieved in human trials for sickle cell disease to date (337 nM [Ataga K I, Orringer E P, Styles L, Vichinsky E P, Swerdlow P, Davis G A, DeSimone P A, Stocker J W. 2006. Dose-escalation study of ICA-17043 in patients with sickle cell disease. Pharmacotherapy 26:1557-1564]). However, in unpublished industry safety data in primates, daily doses of 1,000 mg/kg yielding a peak serum concentration of 5.3 M were well tolerated for 9 months. Canines developed cardiotoxicity when serum concentrations exceeded 18 M (Douglas Krafte, Pfizer, Inc., unpublished data). Thus, animal studies demonstrate that senicapoc is safe at high doses.

Senicapoc, a Gardos channel inhibitor, prevented erythrocyte dehydration in clinical trials of patients with sickle cell disease. The inventors tested the hypothesis that senicapoc-induced blockade of the Gardos channel inhibits *Plasmodium* growth. Senicapoc inhibited in vitro growth of human and primate plasmodia during the clinical blood stage. Senicapoc treatment suppressed *P. yoelii* para-sitemia in vivo in C57BL/6 mice. The reassuring safety and biochemical profile of senicapoc encourage its use in antimalarial development. The in vitro data disclosed herein support the concept of antimalarial activity of senicapoc through a mechanism independent of the Gardos channel. Without wishing to be bound by a theory, other ion channels may be involved in the mechanism of the drug since senicapoc appears to inhibit intracellular growth of the parasite.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A method for treating malaria, comprising administering to a subject in need thereof a therapeutically effective amount of a potassium channel inhibitor, wherein the potassium channel inhibitor is a compound of Formula (I):

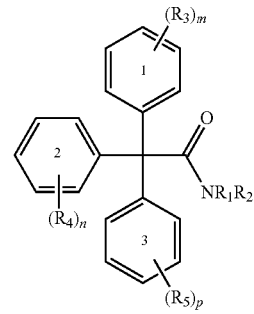

Formula (I)

wherein:

m, n and p are independently 0 or 1, provided that at least one of m, n and p is 1;

$R_1$ and $R_2$ are independently H or alkyl;

$R_3$, $R_4$ and $R_5$ are independently halogen, alkyl, alkenyl, alkynyl or alkoxy; and any stereoisomer, solvate or pharmaceutically acceptable salt thereof.

2. The method of claim 1, wherein at least two of m, n and p are 1.

3. The method of claim 2, wherein all three of m, n and p are 1.

4. The method of claim 1, wherein $R_1$ and $R_2$ are independently H or $C_1$-$C_6$ alkyl.

5. The method of claim 4, wherein $R_1$ and $R_2$ are independently H, methyl, ethyl or propyl.

6. The method of claim 5, wherein $R_1$ and $R_2$ are H.

7. The method of claim 1, wherein at least one of $R_3$, $R_4$ and $R_5$ is a halogen.

8. The method of claim 1, wherein at least one of $R_3$, $R_4$ and $R_5$ is an alkyl.

9. The method of claim 1, wherein at least one of $R_3$, $R_4$ and $R_5$ is an alkoxy.

10. The method of claim 1, wherein $R_3$, $R_4$ and $R_5$ are independently halogen, $C_1$-$C_6$alkyl or $C_1$-$C_6$alkoxy.

11. The method of claim 10, wherein $R_3$, $R_4$ and $R_5$ are independently F, Cl, methyl or methoxy.

12. The method of claim 1, wherein the compound is of Formula (II):

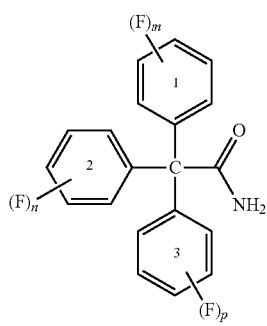

Formula (II)

wherein:
m, n and p are independently 0 or 1, provided that at least one of m, n and p is 1; and
any stereoisomer, solvate or pharmaceutically acceptable salt thereof.

13. The method of claim 12, wherein the compound is of Formula (III):

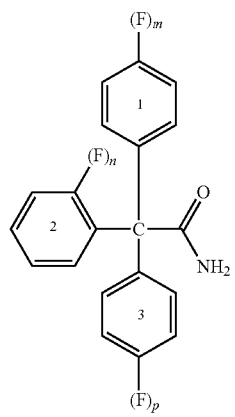

Formula (III)

wherein:
m, n and p are independently 0 or 1, provided that at least one of m, n and p is 1; and
any stereoisomer, solvate or pharmaceutically acceptable salt thereof.

14. The method of claim 1, wherein the compound is of Formula (IV):

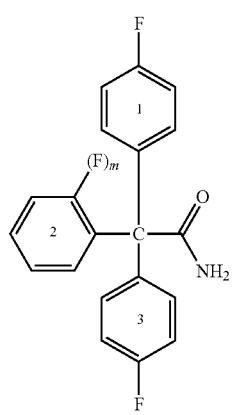

Formula (IV)

wherein:
m is either 0 or 1; and
any stereoisomer, solvate or pharmaceutically acceptable salt thereof.

15. The method of claim 1, wherein the potassium channel inhibitor is selected from the group consisting of:

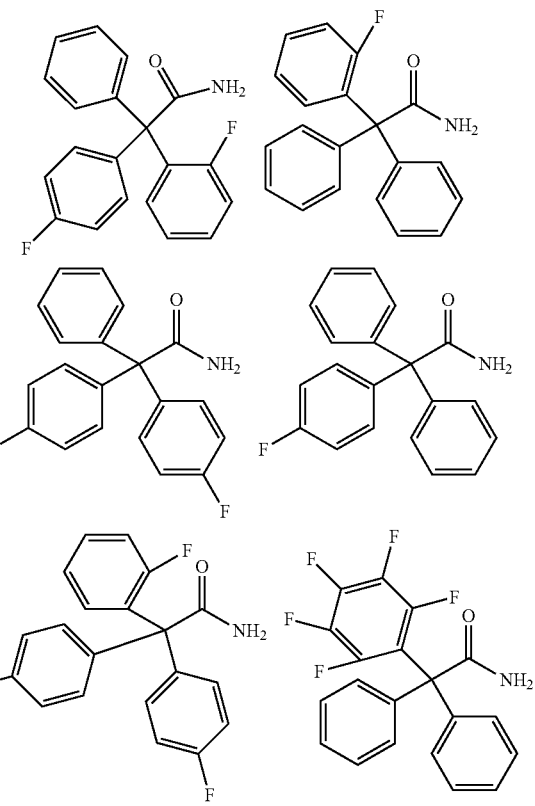

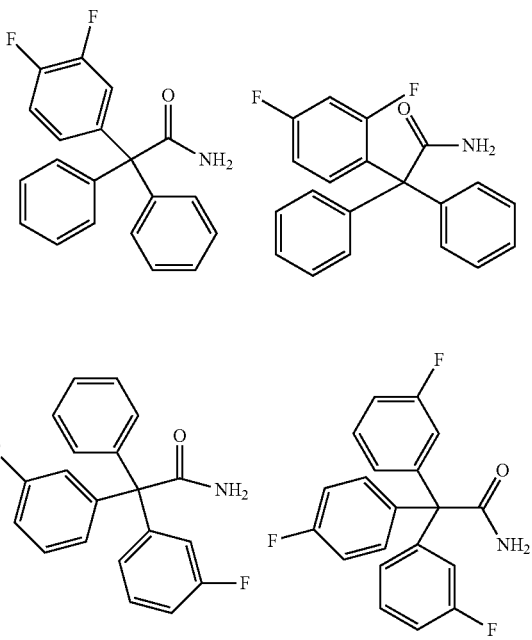

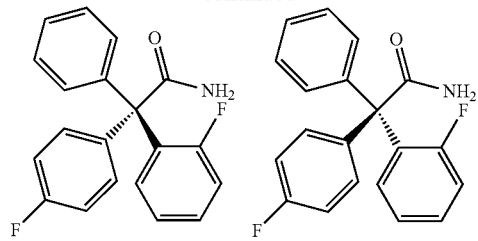

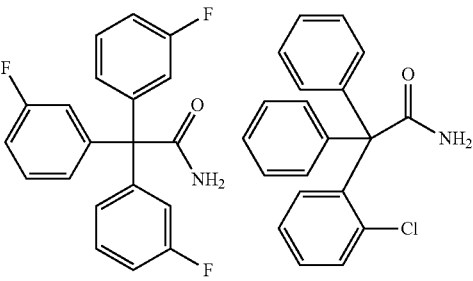

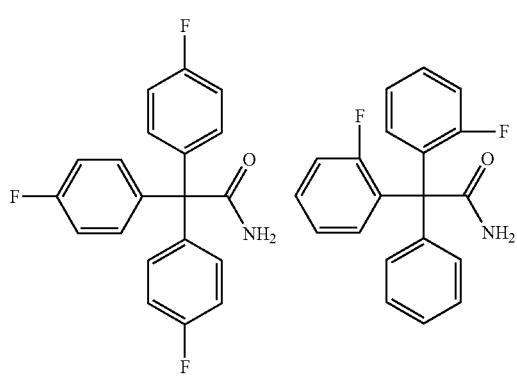

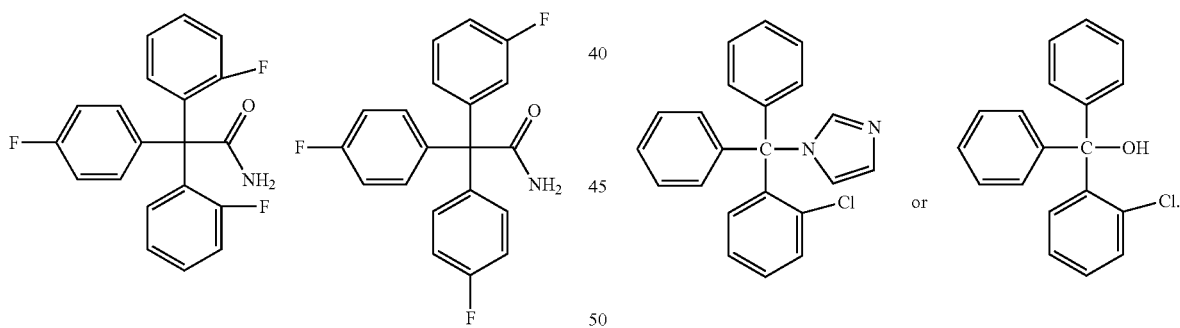

and any stereoisomer, solvate or pharmaceutically acceptable salt thereof.

16. The method of claim 1, wherein the potassium channel inhibitor is senicapoc (2,2-bis(4-fluorophenyl)-2-phenylacetamide).

17. A method for treating malaria, comprising administering to a subject in need thereof a therapeutically effective amount of a potassium channel inhibitor, wherein the potassium channel inhibitor is

* * * * *

UNITED STATES PATENT AND TRADEMARK OFFICE
CERTIFICATE OF CORRECTION

PATENT NO. : 10,179,115 B2
APPLICATION NO. : 15/552027
DATED : January 15, 2019
INVENTOR(S) : Venee Tubman and Carlo Brugnara It is certified that error appears in the above-identified patent and that said Letters Patent is hereby corrected as shown below:

In the Specification

At Column 1, Lines 16-21:
"This invention was made with Government support under grant no. T32 HL007574 awarded by the National Heart, Lung, and Blood Institute (NHBLI) and grant no. R01 AI091787 awarded by the National Institute of Allergy and Infectious Diseases (NIAID). The government has certain rights in the invention."

Should be replaced with:
--This invention was made with government support under Grant Number AI091787, awarded by the National Institutes of Health. The government has certain rights in the invention.--

Signed and Sealed this
Fifth Day of September, 2023

Katherine Kelly Vidal
*Director of the United States Patent and Trademark Office*